United States Patent [19]

Kauvar et al.

[11] Patent Number: 5,155,049
[45] Date of Patent: Oct. 13, 1992

[54] BLOTTING TECHNIQUE FOR MEMBRANE ASSAY

[75] Inventors: Lawrence M. Kauvar; Peter Y.K. Cheung, both of San Francisco, Calif.

[73] Assignee: Terrapin Technologies, Inc., San Francisco, Calif.

[21] Appl. No.: 396,865

[22] Filed: Aug. 22, 1989

[51] Int. Cl.⁵ .............................................. G01N 33/00
[52] U.S. Cl. .................................. 436/177; 204/180.1; 422/101; 436/518; 436/807
[58] Field of Search ................... 422/56, 57, 58, 101, 422/102; 436/57, 86, 177, 807, 513, 518; 435/6, 7, 805, 810; 204/180.1, 299 R, 409

[56] References Cited

U.S. PATENT DOCUMENTS

| | | | |
|---|---|---|---|
| 4,314,897 | 2/1982 | Monte et al. | 422/102 |
| 4,366,241 | 10/1982 | Tom et al. | 435/7 |
| 4,427,415 | 1/1984 | Cleveland | 436/57 |
| 4,632,901 | 12/1986 | Valkirs et al. | 435/5 |
| 4,704,255 | 11/1987 | Jolley | 422/102 |
| 4,826,759 | 5/1989 | Guire et al. | 422/58 |

OTHER PUBLICATIONS

"Molecular Cloning, A Laboratory Manuel" T. Maniatis et al. (Cold Spring Harbor Laboratory: New York) 1982 pp. 383–386.
Hoefer Scientific Instruments, Publication, Transfer Electrophoresis, Hybrid-Ease advertisement, pp. 60–61.

Primary Examiner—Jill A. Johnston
Attorney, Agent, or Firm—Morrison & Foerster

[57] ABSTRACT

A technique for passaging liquid through a membrane putatively containing, in its interstices, at least one substance for which detection is desired, comprises positioning donor and acceptor bibulous matrices onto either surface of the membrane and squeezing the resulting sandwich. This technique permits the application of small volumes of reagents or wash to the membranes and the facile recovery of the waste. The subject membranes are obtained, for example, by blotting developed electrophoresis gels or directly by their use as supports for specific binding assays.

16 Claims, 2 Drawing Sheets

NO WASH

3 WASHES

BLOTTING TECHNIQUE FOR MEMBRANE ASSAY

TECHNICAL FIELD

The invention relates to laboratory techniques for detecting the positions of or presence/absence of substances which are putatively contained in membrane interstices. More particularly, it concerns a blotting technique for applying reagents and wash solutions to accomplish this detection.

BACKGROUND ART

There are a number of instances in which it is desirable to detect the presence and/or location of substances embedded in a membrane.

For instance, such membranes are used to obtain replicas of developed gel electrophoresis supports. The use of gel electrophoresis is currently a ubiquitous technique for the separation of biological materials. (Nonbiological materials can be separated using gels or other chromatographic supports as well, but the scope of effort with regard to biologicals is very great.) Typical applications include separation of nucleic acid fragments of various sizes either in the context of sequence determination; in the detection of polymorphisms; or verification of sizes in other contexts. Also frequently conducted are separations of proteins and glycoproteins and application of gel separations as verification of homogeneity or purity. In all of these procedures samples are applied to gels and the components are separated by application of an electric field across the gel. Regardless of the manner in which the gel is developed, the resulting pattern of migration of the substances contained in the sample must be visualized in some manner.

To conduct this visualization, typically the gel support is contacted with a membrane to which the substances will be transferred in the same pattern in which they appeared on the gel. The "spots" are then visualized by, at a minimum when the substances are labeled, washing the membrane to remove background contaminants. In most cases detection is by adding to the membrane detecting reagents which react with the substances to be detected and then washing the excess away.

The present procedures, for applying and removing these reagents and for washing away contaminants involve substantial volumes of fluid and are difficult to conduct. The typical procedure for applying reagent or wash is to immerse the membrane in a liquid and agitate the liquid bath. The membrane is removed from the bath and excess liquid drained off. Alternatively, the wash solutions are withdrawn using a vacuum. This procedure is disclosed, for example, in U.S. Pat. No. 4,427,415. This procedure takes a good deal of time and requires large volumes of solution. Furthermore, the vacuum application tends not to result in an evenly applied pressure gradient so that large surface areas do not behave well under this protocol. The result is that the design of systems for vacuum application has been limited to small areas such as those associated with spot testing on, for example, a microtiter plate, e.g., the Dot-Blot system marketed by Bio-Rad. This type of spot test is another instance in which visualization of substances embedded in membranes is required, as explained below.

A recent effort to overcome the problems of large volumes and uneven vacuum pressure is exemplified in the Hybrid-Ease TM hybridization chamber marketed by Hoefer Scientific Instruments. This chamber comprises two grids between which the membrane is sandwiched. The grid plates are snapped into position surrounding the membrane, and syringes fitted into the open space created by the grids. One syringe is used to apply reagents and wash, and the other to withdraw excess. This system still requires large volumes of liquid and is cumbersome to employ.

Bibulous materials have been used in other contexts to draw fluids through membranes where only the presence, absence or amount of a material at a known location is to be determined. For example, immunoassay procedures, such as those described in Syva U.S. Pat. No. 4,366,241 and Hybritech U.S. Pat. No. 4,632,901, use the capillary action of an absorbent material to draw fluids through a reaction-supporting membrane.

It is clear that a more efficient method for detection of the migration patterns resulting from electrophoresis on supporting gels or for general assay procedures is required. The present invention permits a more efficient elucidation of the migration pattern as replicated on a transfer membrane, and more effective detection of results of specific binding reactions on solid supports.

DISCLOSURE OF THE INVENTION

A rapid, efficient and convenient method to detect the pattern, nature or amount of substances on a membrane is provided. The invention method involves a simple positive-pressure squeeze-blotting procedure which effectively supplies and removes reagents and permits washing of the contaminants from substances embedded in the membrane to be detected using very low volumes of liquid.

Thus, in one aspect, the invention is directed to a method to passage liquid, such as a reagent solution or wash, through a membrane in which substances to be detected are embedded. The membrane may, for example, correspond to the migration pattern of a sample subjected to separation on a solid support. The membrane may also be a specific-binding assay solid support. The method comprises positioning a donor bibulous matrix containing the liquid to be supplied onto one surface of the membrane, and an acceptor bibulous matrix on the opposite surface of the membrane. The resulting "sandwich" is then squeezed by application of even positive pressure over the surface on both sides, and the liquid is forced from the donor matrix through the membrane onto the acceptor matrix. This method is particularly useful for membranes that are obtained by blotting of a gel support which has been used for electrophoretic separation of materials contained in a sample or verification of purity.

In another aspect, the invention is directed to an apparatus useful in conducting the method of the invention.

MODES OF CARRYING OUT THE INVENTION

Figure 1A:
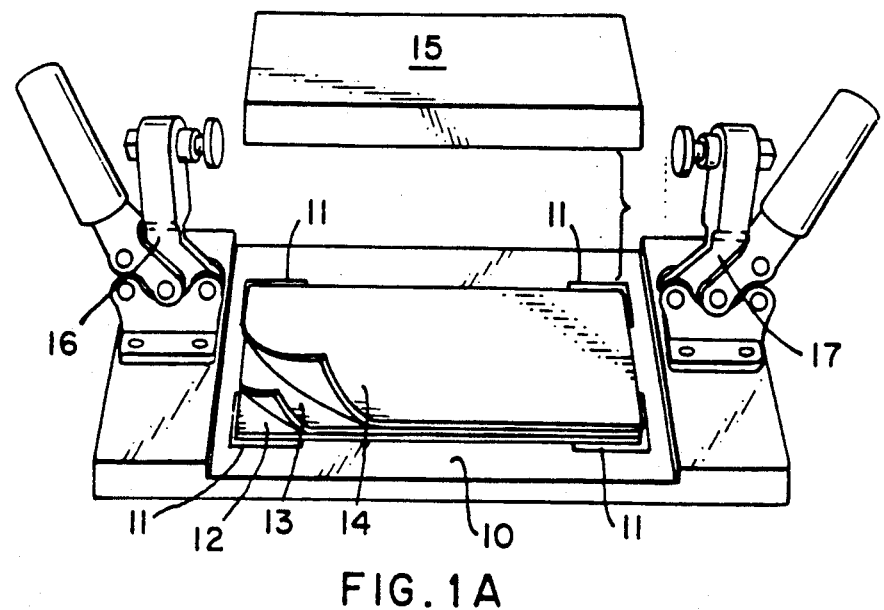
FIGS. 1A-1C show a perspective view of the apparatus of the invention absent and present the application of pressure, respectively.

The invention relates generally to the technique of passing liquids through membranes by means of a sandwich arrangement wherein the membrane has positioned on one of its surfaces a donor bibulous matrix which contains the liquid, and on the other, opposing, surface an acceptor bibulous matrix which contains substantially no fluid. The resulting sandwich, when compressed using positive pressure results in the transfer of the liquid from the donor matrix through the membrane to the acceptor matrix. The sandwich can be held in place for any desired period, e.g., 30 minutes to 24 hours, resulting in a corresponding period of incubation of the membrane contents with the liquid and the solutes it contains. Simple washing can be conducted in this manner as well; in this case no substantial holding period is required.

In a less preferred embodiment, the donor matrix may first be positively pressed onto the membrane without the acceptor matrix. This step may be followed, optionally, by pressing the acceptor matrix against the other side of the membrane, or by removal of the donor matrix followed optionally by compression against the acceptor matrix placed against either side of the membrane. This embodiment is less preferred because the membrane itself often has no holding capacity, and thus washing, for example, by this protocol is not very effective.

The membrane contains, in its interstices, one or more substances to be detected. Generally these substances are present in the interstices either by virtue of having been blotted from a solid support for electrophoresis or chromatography or by direct application, usually to detect the presence, absence, or amount of a particular type of material such as an antibody or specific protein—i.e., a Dot-Blot type assay. The definition of the membrane is not limited, however, to these instances, but applies to any case wherein a membrane contains in its interstices one or more substances to be detected. Included in the types of membranes envisioned are paper chromatographic strips, membranes commonly used to blot electrophoresis gels such as nitrocellulose; nylon; membranes of proprietary composition such as that marketed under the trademark Immunodyne TM; or various other polymeric membranes, such as polyvinyl difluoride, marketed under the trademark Immobilon TM. A variety of materials can be used to replicate the results of electrophoresis gels performed on various samples as is understood in the art. Most commonly, the samples contain biological substances such as individual proteins, antibodies, nucleic acids, oligonucleotides, complex carbohydrates, and the like, but the application of the technique is not limited to membranes containing these substances. The invention technique is applicable to any membrane containing within its interstices a substance to be detected regardless of the chemical composition of the membrane or of the target substances.

When membranes which represent replicas of electrophoretic results are employed, the transfer of the substances to be detected from the gel to the membrane can be conducted by utilizing membranes containing transfer buffer, by electroelution, or by dry blotting of the gels. Techniques for these transfers are well understood in the art, and do not constitute part of the invention herein.

Another major type of membrane utilized in current work is the Dot-Blot type membrane which permits the impregnation of multiple samples on the same experimental surface. Typical configurations of dot blots include those which approximate microtiter plates.

Other suitable membranes include those which are directly used themselves as chromatographic supports.

The donor and acceptor bibulous matrices can be made of a variety of materials as well. Because the transfer of liquid from donor matrix to membrane and from membrane to acceptor matrix is conducted under positive pressure, restriction on the relative pore sizes of the membrane and matrices is not of great importance. The donor matrix must be bibulous in the sense that it is able to retain, absent the application of pressure, or absent contact with a matrix of smaller pore size, sufficient liquid to conduct the procedure described for detection of substances in the membrane. Similarly, the acceptor matrix must be sufficiently bibulous to absorb the liquid from the membrane under applied pressure. Suitable matrices of the invention include cellulosic filter paper, as well as other woven or spongelike materials. (Typically, bibulous materials are capable of retaining fluid volumes of at least 0.1 ml/cm$^2$, but the "bibulousness" required varies with the application.) Generally the donor and acceptor matrices are sufficiently planar to be considered two dimensional, but thicker "block" forms of these materials can also be used.

The liquid to be supplied may contain detecting reagent or may simply be provided as a wash. The nature of the detecting reagent depends, of course, on the substance to be detected. Typically, proteins are detected by immunological reactions between antigen and antibody or immunoreactive portions thereof; typically the presence of nucleic acid fragments is detected by suitable oligonucleotide probes. The detecting substances responsible for the immediate or specific reaction with the substance to be detected may be further supplemented, if needed, with label and a multiplicity of applications of the detecting reagents may be needed—e.g., a protocol may include detection of an antigen by supplying an antibody labeled with an enzyme, e.g., commonly, horseradish peroxidase, and then this binding is detected by means of supplying substrate for this enzyme. In application of reagent, it is possible, though not preferred, to use only a positively pressed donor matrix to expose this component of the membrane for a defined period.

The membrane is typically washed after the application of each detecting reagent; the wash solutions are applied using the method of the invention, wherein both donor and acceptor membranes are compressed in a "sandwich," as it is desirable for the wash to passage through the membrane. The wash technique of the invention requires only surprisingly small volumes of wash liquid to be effective.

It is most convenient to conduct the method of the invention at room temperature, but elevated and lower temperatures can also be used. These can be effected by thermostatting the apparatus, or by preheating or cooling the means for applying pressure.

Figure 1B:
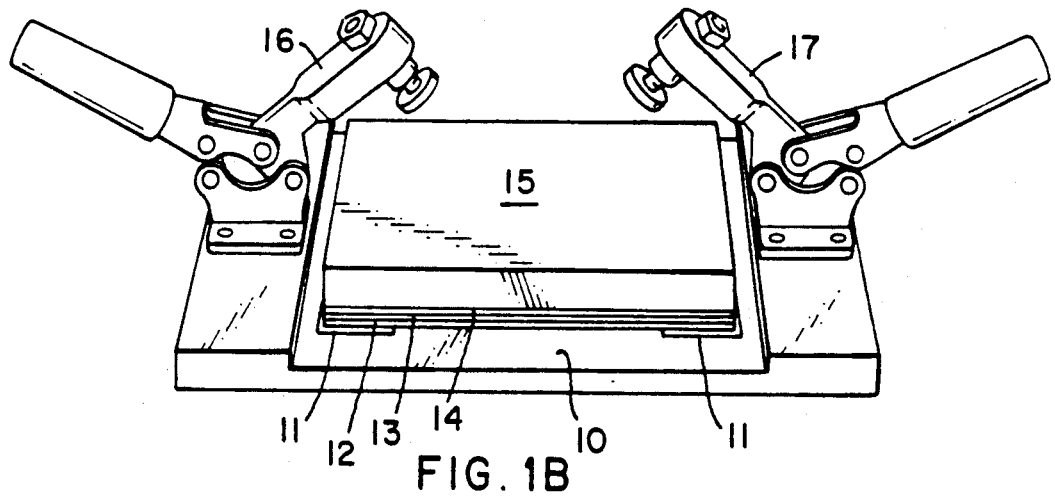
Figure 1C:
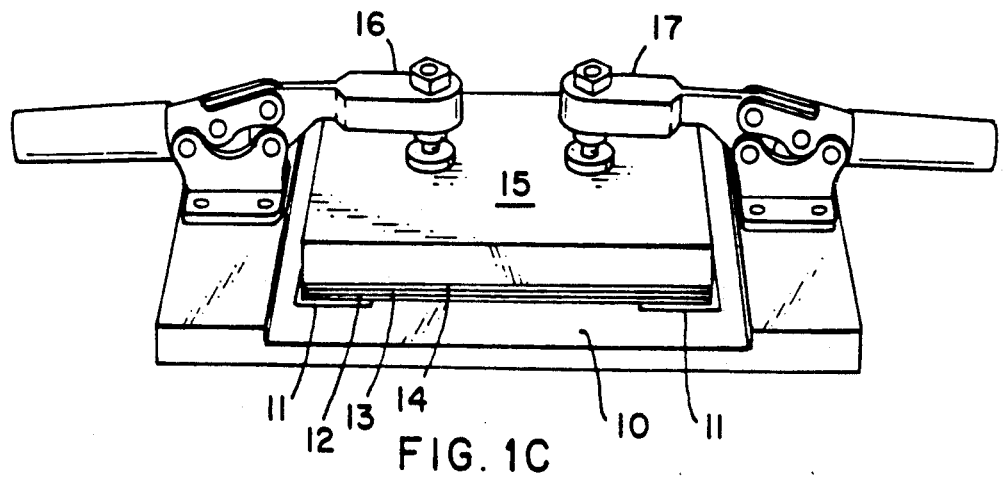

The apparatus in which the method of the invention is conducted must contain a means for positioning each of the matrices at the surface of the membrane and a means for applying even pressure to the membrane in contact with the matrices. One preferred embodiment is shown in FIGS. 1A–1C. As shown in FIG. 1A, a cradle 10 contains a delineated surface for positioning of the matrix and membrane. The positioning means 11, which in this case is simply a line indication of where to place the matrix/membrane sandwich, is covered first with the acceptor matrix 12, then with the membrane 13, and then with the donor matrix 14. The pressure plate 15 is available to mediate even the application of positive pressure. Pressure providing means, 16 and 17, are in the open position. These pressure application means are standard pressure clamps which are commercially available.

FIG. 1B shows pressure plate 15 in position, prior to application of pressure.

FIG. 1C shows this apparatus when pressure is being applied. The pressure mediating plate 15 is placed on top of the matrix/membrane/matrix sandwich and the pressure providing devices 16 and 17 are readjusted to supply pressure. Within only a few seconds, the transfer of liquid contained in the donor matrix to acceptor matrix is complete.

The temperature of the blotting can be regulated by applying or subtracting heat from the cradle 10 and/or the pressure mediating plate 15.

It should be noted that the foregoing is simply an illustrative design. The positioning means is arbitrary; it can be a raised frame, a delineated surface, or, in some cases, the judgment of the operator. The pressure application means may include, instead of pressure plate 15, rollers which traverse the surface, either individually in counterpart to a supporting surface on the other side of the matrix/membrane composite, or in a laundry wringer type arrangement. Any means of applying even, positive pressure may be used.

EXAMPLES

The following examples are intended to illustrate but not to limit the invention.

EXAMPLE 1

Dot-Blots of IgG and KLH

Figure 2:
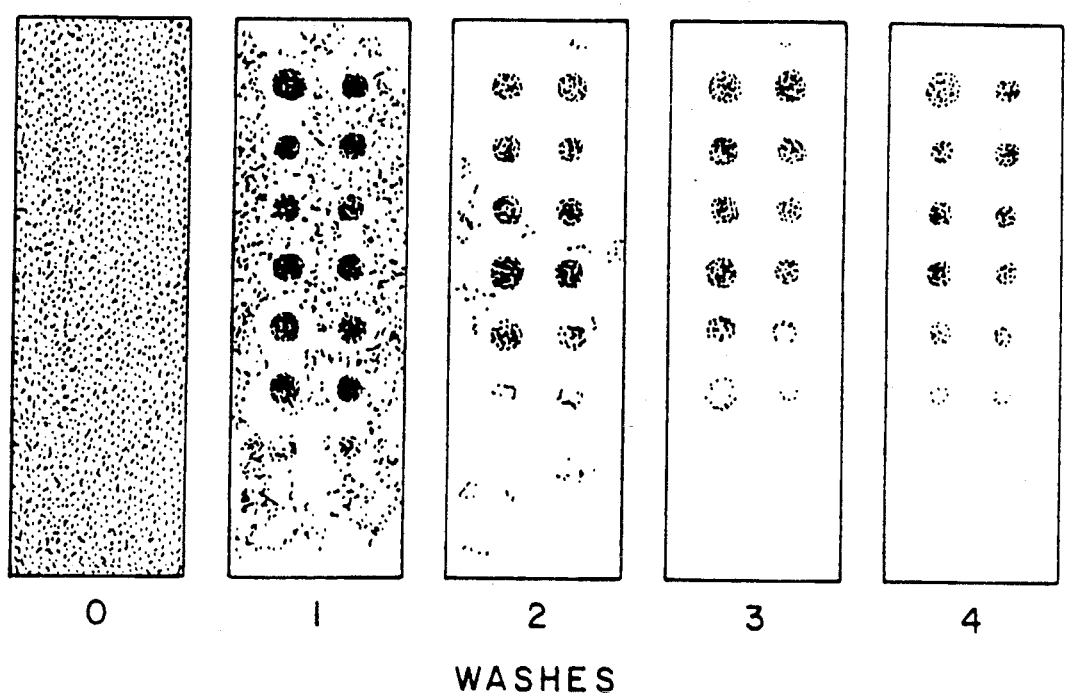
FIG. 2 shows results of successive washings using Dot-Blots of IgG and KLH.

Dot-Blots were obtained by spotting labeled IgG or labeled KLH at several dilutions from 4 ug/dot to 0.062 ug/dot using Immobilon TM membranes. FIG. 2, rows (1)-(4), show the results of successive washing conducted with the apparatus of FIG. 1 using filter paper matrices saturated with wash buffer.

EXAMPLE 2

Western Blot of Immunoglobulins and KLH

A. SDS-polyacrylamide gel electrophoresis of a sample mouse IgG was conducted following standard procedures.

Figure 3A:
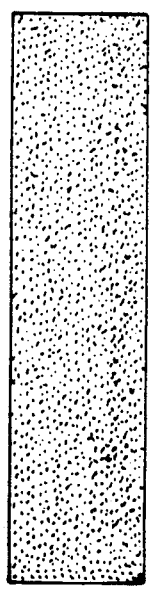
FIGS. 3A-3B shows the results of three washes using the technique of the invention on Western Blots of IgG.
Figure 3B:
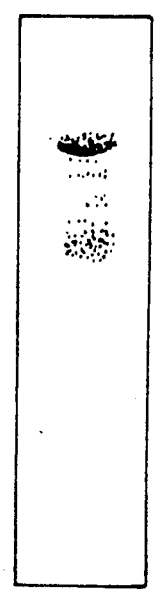

The resulting gel was blotted onto nitrocellulose in a transverse electric field using commercially available tanks. After blotting, the membrane was incubated in a 1% solution of casein to block excess protein-binding sites. This "Western" blot was then exposed to a small volume of HRP-labeled goat antimouse serum. After 3 washes using the apparatus of FIGS. 1A-1C, using filter paper matrices saturated with buffer, the membrane was exposed to HRP substrate. Specific detection of IgG was accomplished, as shown if FIG. 3, where lane A is the un-washed membrane and lane B is a corresponding washed membrane.

B. Using the procedure of paragraph A, SDS-polyacrylamide gel electrophoresis was performed using various antibodies and antigens, including anti-KLH and anti-fluorescein, alone or mixed, and yeast whole cell lysate. The resulting patterns were transferred to various membranes, i.e., Immunodyn TM, Immobilon TM, and nitrocellulose. Detection and washing were conducted as in paragraph A, with comparable results.

We claim:

1. A method to pass a wash- or reagent-containing liquid through a single membrane, which membrane is a replica of a developed gel electrophoresis support, which replica putatively contains, in its interstices, at least one substance for which detection is desired, wherein the method comprises:

positioning a donor bibulous matrix containing said liquid onto one surface of the replica putatively containing said substance in its interstices and positioning an acceptor bibulous matrix on the opposite surface of the replica to form a sandwich; and squeezing or pressing by applying positive mechanical pressure to both sides of the sandwich so as to force said liquid from the donor matrix through the replica to the acceptor matrix while retaining substantially all of said substance in the interstices of the replica and detecting the presence or absence of said at least one substance in said replica.

2. The method of claim 1 wherein the donor and acceptor bibulous matrices are filter paper.

3. The method of claim 1 wherein the liquid is a wash solution.

4. The method of claim 1 wherein the liquid contains a reagent for detecting said at least one substance contained in the interstices of the replica.

5. The method of claim 4 wherein said at least one substance is selected from the group consisting of nucleic acids and proteins.

6. A method to expose a single membrane, which membrane is a replica of a developed gel electrophoresis support, which replica putatively contains, in its interstices, at least one substance for which detection is desired, to a liquid containing a detection reagent, wherein the method comprises:

positioning a donor bibulous matrix containing said liquid onto one surface of the replica putatively containing said substance in its interstices; followed by squeezing or pressing by applying positive mechanical pressure to said donor bibulous matrix so as to force said liquid onto the replica; optionally followed by positioning an acceptor bibulous matrix on either surface of the replica so that liquid is caused to flow from the replica to the acceptor matrix while retaining substantially al of said substance in the interstices of the replica and detecting the presence or absence of said at least one substance in said replica.

7. The method of claim 6 wherein the acceptor matrix is positioned on the surface of the replica opposite that of the donor matrix.

8. The method of claim 6 wherein the liquid is caused to flow from the replica to the acceptor matrix by application of positive mechanical pressure to the surface of the replica.

9. A method to pass a wash- or reagent-containing liquid through a single membrane, which membrane is a multiple dot type assay solid support which support putatively contains, in its interstices, at least one substance for which detection is desired, wherein the method comprises:

positioning a donor bibulous matrix containing said liquid onto one surface of the support putatively containing said substance in its interstices and positioning an acceptor bibulous matrix on the opposite surface of the support to form a sandwich; and squeezing or pressing by applying positive mechanical pressure to both sides of the sandwich so as to force said liquid from the donor matrix through the support to the acceptor matrix while retaining substantially all of said substance in the interstices of the support and detecting the presence or absence of said at least one substance in said support.

10. The method of claim 9 wherein the donor and acceptor bibulous matrices are filter paper.

11. The method of claim 9 wherein the liquid is a wash solution.

12. The method of claim 9 wherein the liquid contains a reagent for detecting the substances contained in the interstices of the support.

13. The method of claim 12 wherein said substances are nucleic acids or proteins.

14. A method to expose a single membrane, which membrane is a multiple dot type assay solid support, which support putatively contains, in its interstices, at least one substance for which detection is desired, to a liquid containing a detection reagent, wherein the method comprises:

positioning a donor bibulous matrix containing said liquid onto one surface of the support putatively containing said substance in its interstices; followed by squeezing or pressing by applying positive mechanical pressure to said donor bibulous matrix so as to force said liquid onto the support; optionally followed by positioning an acceptor bibulous matrix on either surface of the support so that liquid is caused to flow from the support to the acceptor matrix while retaining substantially all of said substance in the interstices of the support and detecting the presence or absence of said at least one substance in said support.

15. The method of claim 14 wherein the acceptor matrix is positioned on the surface of the support opposite that of the donor matrix.

16. The method of claim 14 wherein the liquid is caused to flow from the support to the acceptor matrix by application of positive mechanical pressure to the surface of the support.

* * * * *